US005425363A

United States Patent [19]

Wang

[11] Patent Number: 5,425,363
[45] Date of Patent: Jun. 20, 1995

[54] PLUNGE ELECTRODE FOR RECORDING MULTIPLE INTRAMYOCARDIAL MONOPHASIC ACTION POTENTIAL

[76] Inventor: Yong G. Wang, 7445 Roosevelt Rd., Apt. 6, Forest Park, Ill. 60130

[21] Appl. No.: 169,670

[22] Filed: Dec. 17, 1993

[51] Int. Cl.⁶ .......................................... A61B 5/0492
[52] U.S. Cl. ...................................... 128/642; 128/696
[58] Field of Search ............... 128/642, 696; 607/116, 607/119, 122, 129

[56] References Cited

U.S. PATENT DOCUMENTS

| 4,690,155 | 9/1987 | Hess | 607/122 |
|---|---|---|---|
| 4,922,912 | 5/1990 | Watanabe | 607/122 |
| 4,955,382 | 9/1990 | Franz et al. | 128/642 |
| 5,275,162 | 1/1994 | Edwards et al. | 128/642 |

OTHER PUBLICATIONS

"A Method For Recording of Intramyocardial Monophasic Action Potential in Intact Dogs: In Vivo Evidence of M Cells," YG Wang, et al, Pace, vol. 15 (Part II), p. 559, Apr., 1992.
"Construction of A Multipolar Neddle Electrode for Activation Study Of The Heart," Kasell et al, Am J Physiol 233(2) H312-H317, 1977.
"Method and Theory of Monophasic Action Potential Recording," M. R. Franz, Progress in Cardiovascular Disease, vol. 33, No. 6, pp. 347-368, May/Jun., 1991.
"Long-Term Recording of Monophasic Action Potentisls From Human Endocardiam," Franz, Am J Cardiol 51, pp. 1629-1634, 1983.
"Canine Intramyocardial Cells With Long Action Potential Duration," YG Wang et al, Abstracts from the 64th Scientific Sessions, II-179, #0715, 1992.
"Early Afterdepolarizations Arising From M Cells in Intact Dogs," R. J. Hariman et al, Circulation 86(4), 1992 #1199.

Primary Examiner—Lee S. Cohen
Assistant Examiner—Brian M. Green
Attorney, Agent, or Firm—Ladas & Parry

[57] ABSTRACT

A plunge electrode for recording multiple intra-myocardial monophasic action potentials comprises an elongated hollow body with a sharp closed head and an open end and two rows of conductive electrodes provided on opposite sides of the body. One of the electrodes are soldered electrodes and the others are moveable electrodes. The plunge also comprises an adjusting device for adjusting the moveable electrodes between a first position where the moveable electrodes are protruded out of the wall of the body and a second position where the moveable electrode are retracted within the body. Two bundles of conductive wires are respectively connected to said electrodes for transmission of recorded signals.

14 Claims, 6 Drawing Sheets

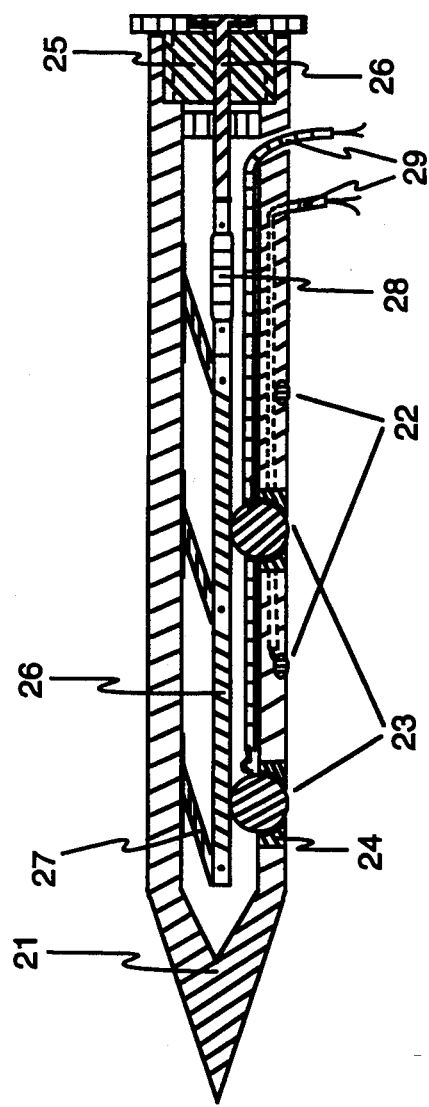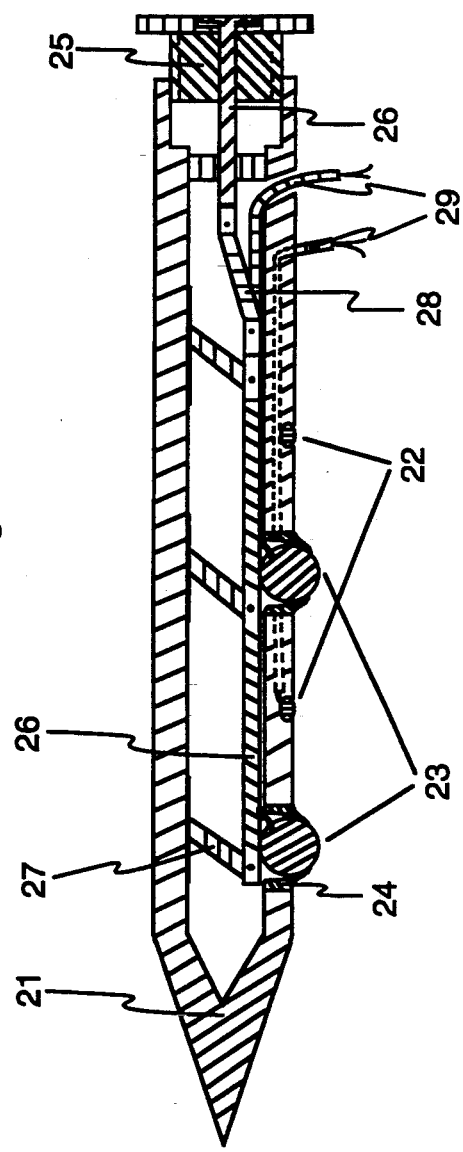
Fig. 4A
Fig. 4B

PLUNGE ELECTRODE FOR RECORDING MULTIPLE INTRAMYOCARDIAL MONOPHASIC ACTION POTENTIAL

The present invention relates to electrodes for recording intramyocardial monophasic action potentials. It relates particularly to a plunge type electrode which is capable of recording multiple intra-myocardial monophasic action potentials in human beings or animals' heart.

BACKGROUND OF THE INVENTION

Monophasic action potentials on epicardial and endocardial surface are conventionally recorded by using section electrodes, contact electrodes, and catheter technique. Those prior art can be seen respectively in articles of (1) "Einphasische Aktionsströme vom in situ durchbluteten Säugetierzen," E. Schütz, Zeitschr Biol 92, pp. 441–452, 1932, (2) "The Monophasic Electrogram Obtained From The Mammalian Heart," K. Jochim et al, Am J Physiol 111, pp. 177–186, 1935, and (3) "Long-Term Recording Of Monophasic Action Potentials From Human Endocardium," M. R. Franz, Am J Cardiol 51, pp. 1629–34, 1983.

In 1992, the present inventor first introduced a needle electrode for recording intramyocardial monophasic action potentials. Such an electrode was described in an abstract of "A Method For Recording Of Intramyocardial Monophasic Action Potential In Intact Dogs: In Vivo Evidence Of M Cells," Y. G. Wang, R. J. Hariman, G. A. Gintant, et al, Pace Vol. 15 (part II), p. 559, April, 1992. Two rows of electrodes of the needle electrode are made of teflon-insulated fine chlorided silver wires. They are inserted into small holes placed along a 16 gauge sheath of a commercially available intravenous catheter (Angiocath). One row electrodes are made into ball-shape. The other row of electrodes are made by trimming the excess wires outside of the sheath. An 18 gauge needle (Abbocath) is used as a stylet inside the sheath to hold the electrodes in place.

However, the tips of both rows of electrodes are outside of the wall of the needle. Thus, they may cause two major problems when the needle electrode is inserted into the ventricular wall. First, the tips may injure the heart seriously. Second, the ball-type tips can be broken easily in the ventricular wall because the wires connecting the small ball tips are very thin. When the needle electrode is being inserted into the ventricular wall, the tips which are outside of the needle, will confront relatively big resistance so as to cause the connecting wires broken. These problems affect the accuracy of recorded data and certainly limit the use of the needle electrode in patients.

Another kind of needle electrode was used by Kasell and Gallagher in 1977 to record ventricular activation in animals and patients. See his article of "Construction Of A Multipolar Needle Electrode For Activation Study Of The Heart," Am J Physiol 233(2) H312–H317, 1977. However, it has only one row of electrodes on one side of the needle electrode. The electrodes are soldered in the wall of the needle. Such a needle electrode is not able to record monophasic action potential.

According to the principle of producing monophasic action potential, the following factors have to be considered in recording intramyocardial monophasic action potential. First, recording monophasic action potential needs bipolar electrodes. Second, the contact of the electrodes with the myocardial tissues must be different, i.e. one is fighter than the other, so that different injury potentials can be produced. Consequently, monophasic action potentials are produced. M. R. Franz describes this principle in his article of "Method and Theory of Monophasic Action Potential Recording," Progress in Cardiovascular Diseases, Vol. 33, No. 6, May/June, 1991, pp. 347–368. Third, it is important to note that, when the electrodes are being inserted into the ventricular wall, the myocardial tissues with which the electrodes contact, should not be seriously injured.

SUMMARY OF THE INVENTION

Therefore, it is an object of this invention to provide a plunge electrode to record accurately multiple intramyocardial monophasic action potentials in animals or patients.

It is another object of this invention to provide a plunge electrode to record monophasic action potentials with less possibility of injury to the myocardial tissues.

According to the present invention, the plunge electrode comprises an elongated hollow body with a closed sharp head and an open end; at least one row of conductive electrodes provided along at least one side of the body, said electrodes including fixed electrodes and moveable electrodes; means for adjusting said moveable electrodes between a first position where said moveable electrodes are partially protruded out of the wall of the body, and a second position where said moveable electrodes are retracted within the body, said adjusting means disposed within the hollow body; and a plurality of conductive wires respectively connected to the electrodes for transmission of recorded signals.

In a preferred embodiment, there are two rows of conductive electrodes provided at opposite sides of the body. One row of electrodes are fixed to the wall of the body. The other row of electrodes are capable of being partially protruded out of and retracted within the body by the adjusting means.

BRIEF DESCRIPTION OF THE DRAWINGS

FIGS. 4A and 4B show another embodiment having only one row of electrodes along one side of the plunge electrode body, but having fixed electrodes alternated with moveable electrodes.

DESCRIPTION OF THE INVENTION

Figure 1:
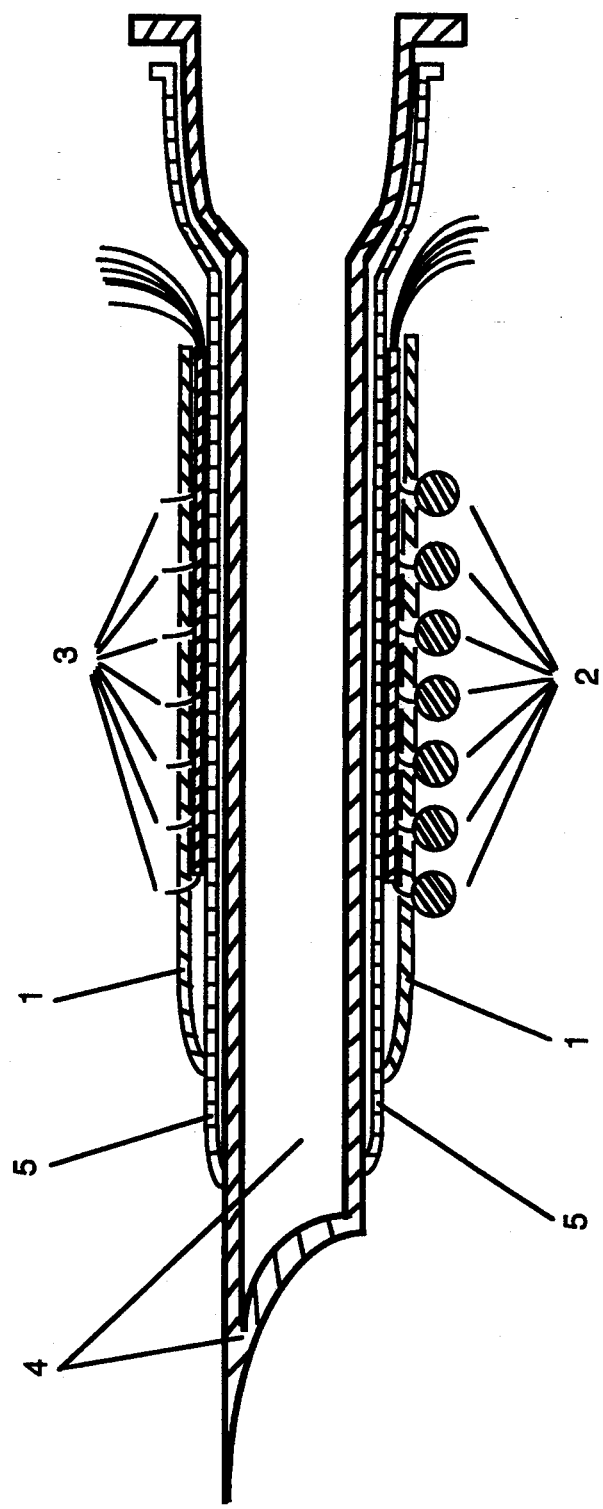
FIG. 1 shows an inventor's early invention of a needle electrode.

FIG. 1 shows the inventor's earlier invention of a needle electrode for recording intramyocardial monophasic action potentials. An outer sleeve or sheath 1, an inner sleeve or stylet 5, and a conventional injection needle 4 are coaxially disposed. Tow bundles of wires connecting respectively electrodes 2 and 3 are provided in a space defined by the outer and inner sleeves 1 and 5. The advantages and disadvantages of this needle electrode have been discussed hereinbefore.

The plunge electrode of the present invention is designed to record simultaneously monophasic action potentials of various myocardial layers or sites from ventricular epicardial surface. Thus, it facilitates the study of electro-physiologic characteristics of transmural cells of the beating heart. It has overcome all drawnbacks of the prior art discussed above.

Figure 2A:
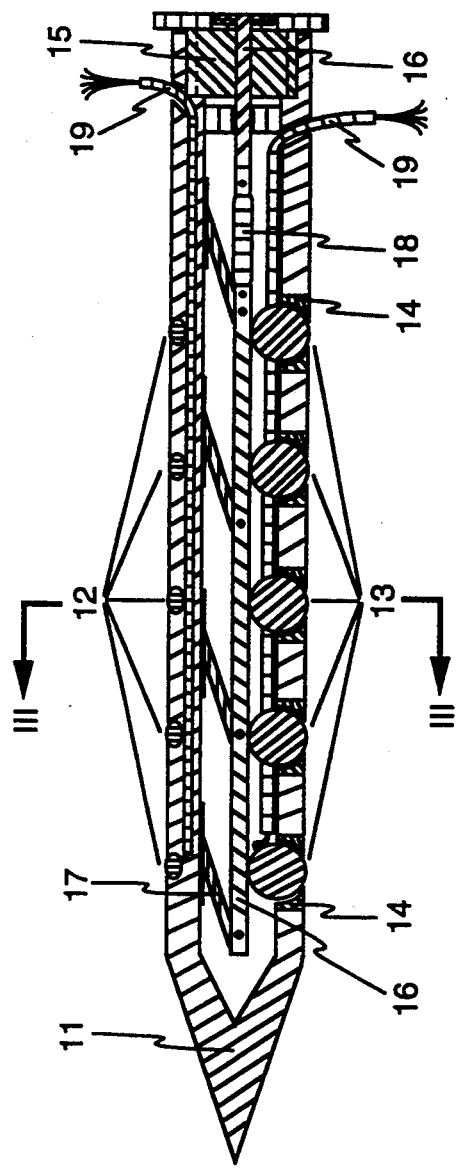
FIG. 2A illustrates the preferred embodiment of this invention with one row of moveable electrodes retracted within the elongated body of the plunge electrode.
Figure 2B:
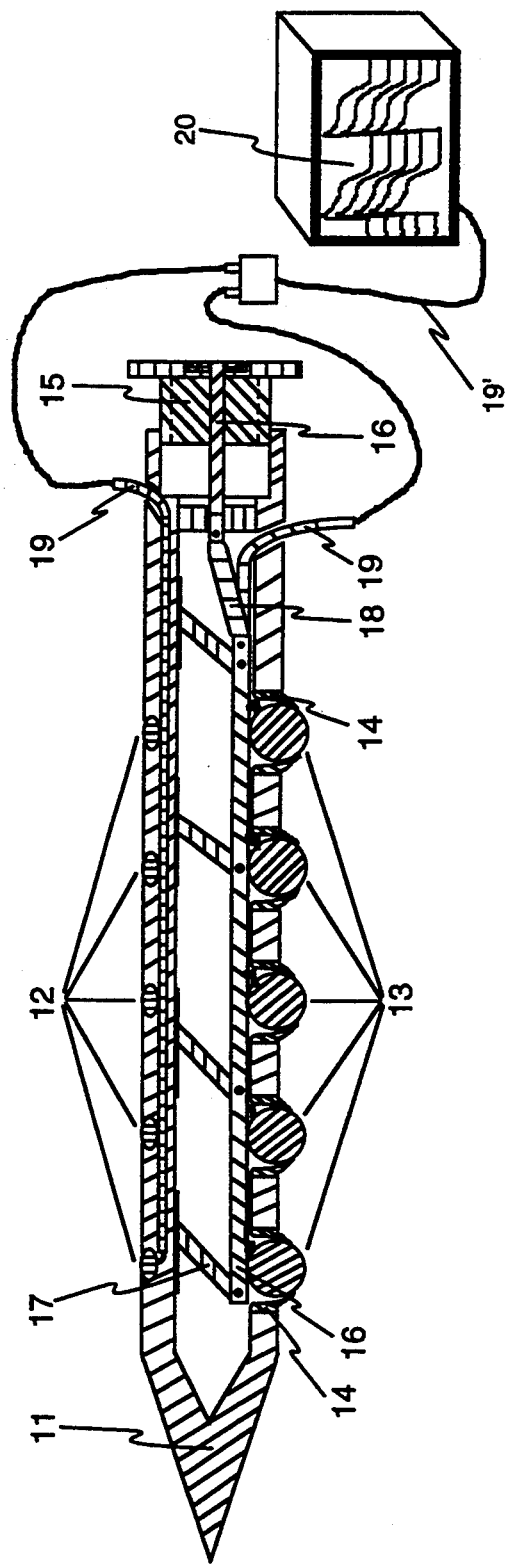
FIG. 2B illustrates the preferred embodiment of this invention with the moveable electrodes partially protruded out of the body of the plunge electrode.

The plunge electrode of this invention is shown in FIGS. 2A and 2B. This plunge electrode comprises an elongated hollow body 11 with a closed sharp head and an open end. The electrode adjusting elements 16, 17, and 18 are disposed within the body 11 through the open end. The plunge body is generally in the shape of a needle or cylindrical, and made of nonpoisonous hard insulation material.

Two rows of electrodes 12 and 13 are provided on opposite sides of the plunge body. The electrodes are made of fine conductive wires coated with insulation material except their out-exposed tips. The size of the tips on both sides of the plunge can be different or same. One row of electrode tips 12 are soldered on the wall of the plunge body. Another row of electrode tips 13 are movable by the adjusting elements. The moveable electrodes 13 can be hidden or retracted in the wall of the plunge body and have a part of their positive camber fit in the small holes 14' formed in the plunge wall, before the plunge electrode is inserted into the ventricular wall as illustrated in FIG. 2A. Each of those small holes 14' is fitted therein with an annular semi-rigid or flexible ring 14. The ring 14 functions as a sealing member to prevent the blood from entering the body. After the plunge electrode is inserted into the ventricular wall, the moveable electrode tips 13 are pushed partially out of the plunge wall through the holes 14' or the annular ring. The moveable electrodes 13 in their protruded position may contact the myocardial tissues tighter than the fixed or soldered electrode tips 12.

As shown in FIG. 2B, the moveable electrodes 13 are protruded by adjusting the screw 15 provided at the end of the plunge body. The screw 15 controls the long actuating rod 16 and several small arms or branches 17. Each of the small branches 17 has one end pivotally attached to the inner wall of the body opposite to the moveable electrodes and another end to the actuating rod 16. The rod has two sections. A longer inner section supports the moveable electrodes. A crank connection bar 18 is provided to connect the two sections of the actuation rod 16, thereby enabling the inner section of the rod 16 to move axially and radially.

When the screw 15 is adjusted, the long rod 16 pushes the electrode tips 13 out of the plunge wall. Therefore, the movable electrode tips 13 may have tighter contact with the local intramyocardial tissues than the soldered electrodes 12. Hence, the different injury potentials between the two rows of electrodes are produced. Accordingly, good monophasic action potentials can be recorded accurately. After the recording is finished, the movable electrode tips 13 will be retracted back into their original position, i.e. within the plunge wall by adjusting the screw 15. The electrode adjusting means can also vary the contact pressure of the electrodes on the myocardial tissues to obtain optimum recording results of the monophasic action potential.

Figure 2D:
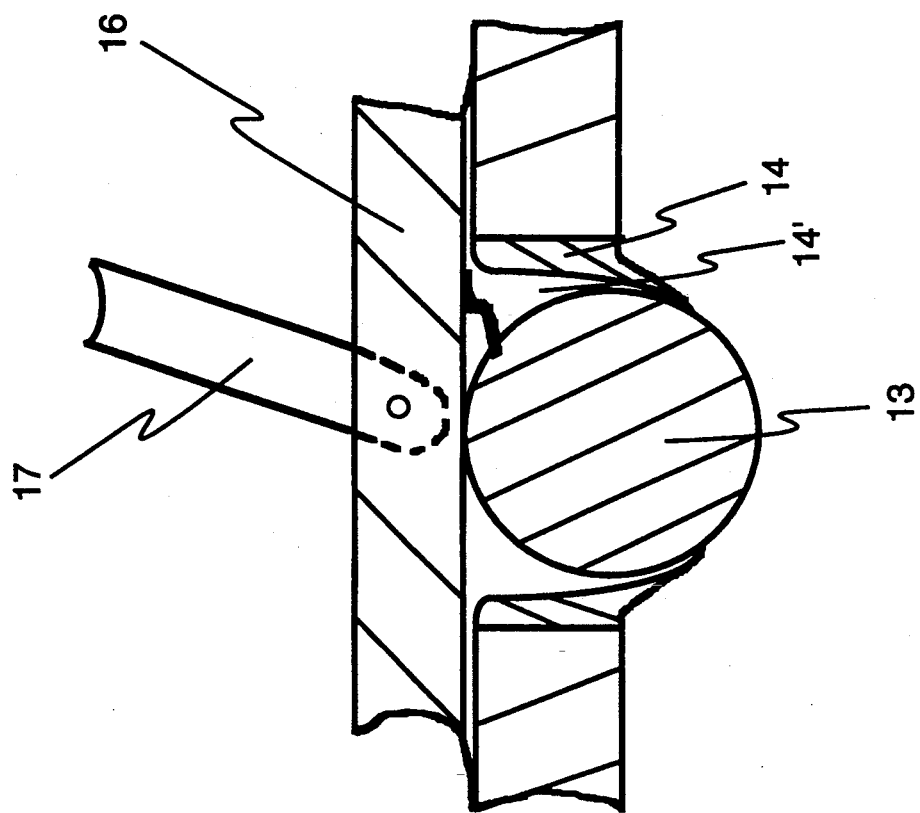
FIGS. 2C and 2D show partial view of the protruded and retracted electrode.
Figure 2C:
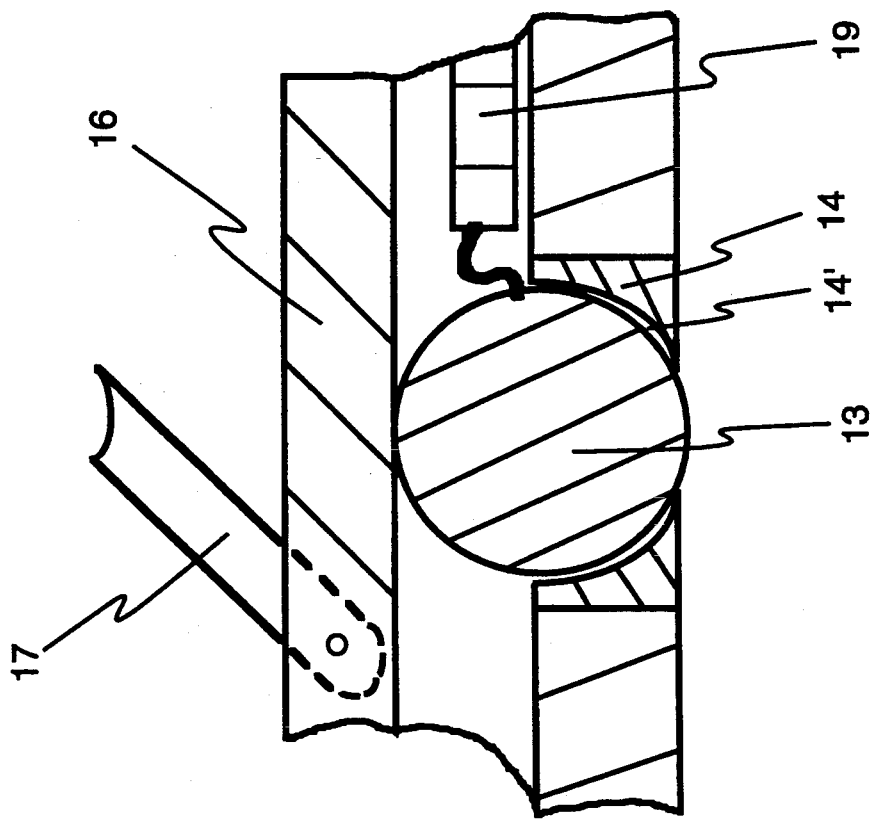
Figure 3:
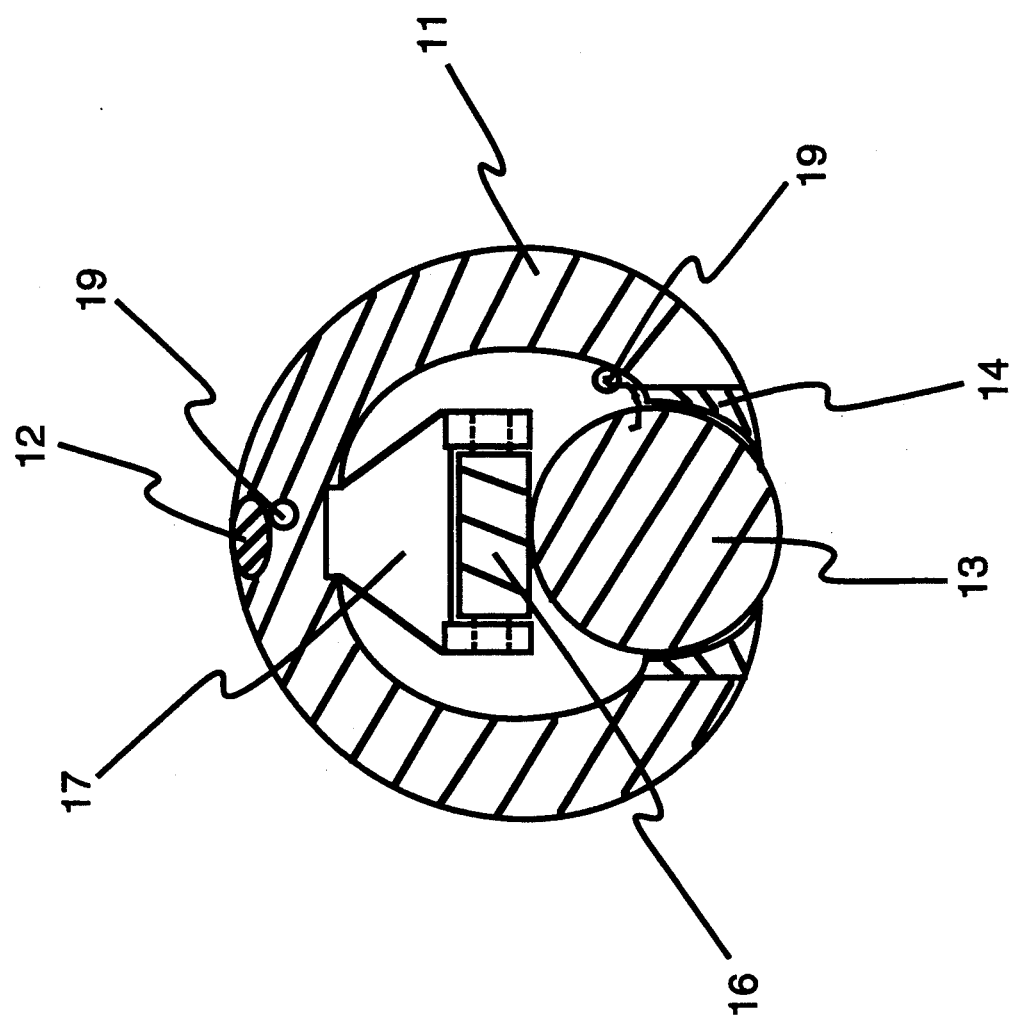
FIG. 3 is a radial cross-section view of this invention taken from III—III line in FIG. 2A.

FIGS. 2C and 2D illustrate the partial view of the moveable electrodes 13 in two different positions. FIG. 3 shows the radial cross-section view of this invention. It illustrates the arrangement of the electrodes 12 and 13 in opposite side walls of the body.

In use, the plunge electrode is inserted perpendicularly into the ventricular free wall. A small nontraumatic clamp (not shown) is then placed on the body of the electrode to hold the plunge in place during the recording of monophasic action potentials. Monophasic action potentials are recorded through the bipolar pairs of electrodes at the same levels, but at opposite sides of the plunge body. The signals recorded thereby are transmitted through the connecting wires 19. Monophasic action potentials at various intramyocardial sites are simultaneously displayed on an oscilloscope and recorded on a chart recorder 20 through a cable 19' in connection with the wires 19. Through each pair of bipolar electrodes, local effective refractory periods can also be measured.

In another embodiment illustrated in FIGS. 4A and 4B, the electrodes 22 and 23 are provided at one side of the plunge body 21. The soldered electrodes 22 are alternated with the moveable electrodes 23. The monophasic action potential can then be measured and recorded between two adjacent soldered and movable electrodes 22 and 23. The advantages of this embodiment is able to reduce the diameter of the plunge body since all electrodes are at one side of the plunge body. However, the monophasic action potential cannot be measured at the same level of local myocardial tissue sites. Nevertheless, this embodiment would have its own application when only one side of myocardial tissues is required to be tested. The adjusting elements 25-28 have the same function of the corresponding parts of the above embodiment.

Figure 5A:
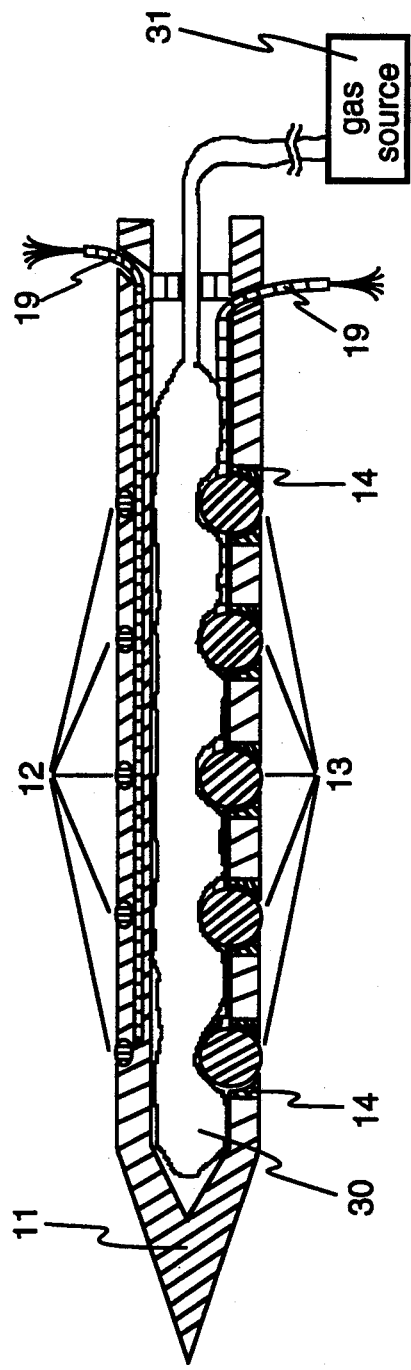
FIGS. 5A and 5B show a further embodiment which uses a gas bag to support and to move the moveable electrodes.
Figure 5B:
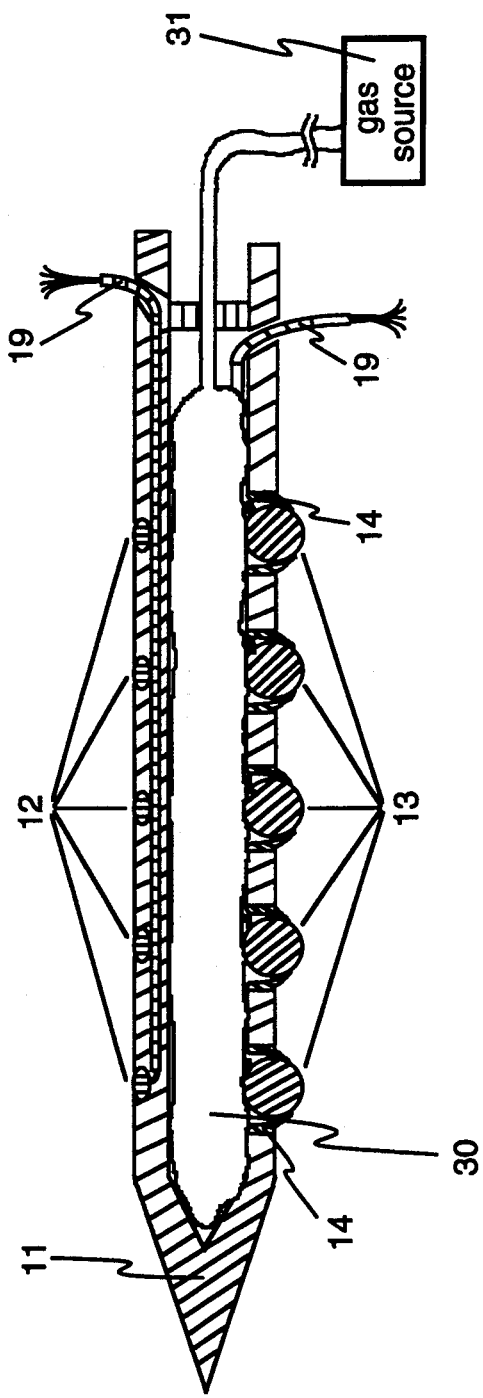

There is a further modified embodiment as shown in FIGS. 5A and 5B, which utilizes a pneumatic adjusting member to replace those adjusting elements 15-18 or 25-28 in the previous embodiments. The pneumatic adjusting member include a gas bag 30 to be filled with controllable gas from an out source 31, which can be any means of providing the controllable gas. The gas bag may support and push out the moveable electrodes to be in the required positions.

In the spirit of the above described invention, it can be understood that a variety of embodiments can be exploited by a person skilled in the art. However, those variation should be within the scope of the accompanying claims of this invention.

What I claim is:

1. A plunge electrode for recording multiple intramyocardial monophasic action potentials, comprising an elongated hollow body with a closed sharp head and an open end; at least one row of conductive electrodes provided along at least one side of the body, said electrodes including fixed electrodes and moveable electrodes; means for adjusting said moveable electrodes between a first position where said moveable electrodes are protruded partially out of a wall of the body, and a second position where said moveable electrodes are retracted within the body, said adjusting means disposed within the hollow body; and a plurality of conductive wires respectively connected to said electrodes for transmission of recorded signals.

2. The plunge electrode of claim 1, wherein there are two rows of said conductive electrodes provided at opposite sides of the body, one row of said electrodes being soldered to the wall of the body and another row capable of being protruded out of and retracted within the body by the adjusting means.

3. The plunge electrode of claim 1, wherein the fixed electrodes and the moveable electrodes are different in size.

4. The plunge electrode of claim 1, wherein the fixed electrodes and the moveable electrodes are of the same size.

5. The plunge electrode of claim 1, wherein said electrode adjusting means include an actuating rod of two sections linked by a crank connection and a plurality of arms with two ends respectively pivotally attached to the actuating rod and an inner wall of the body opposite to the moveable electrodes.

6. The plunge electrode of claim 1, wherein said moveable electrodes are in ball shape and fit respectively in holes formed along the body, each of said holes being fitted with a flexible sealing ring in conformity with the ball shape electrode.

7. The plunge electrode of claim 1, wherein said adjusting means include a gas bag to be filled with controllable gas from an outer source so as to support and push out the moveable electrodes in said positions.

8. A plunge electrode for recording multiple intramyocardial monophasic action potentials, comprising an elongated hollow body with a closed sharp head and an open end; two rows of conductive electrodes provided on opposite sides of the body, one of said rows of conductive electrodes including soldered electrodes and the other being moveable electrodes; means for adjusting said moveable electrodes between at least two positions, said moveable electrodes being protruded partially out of a wall of the body in a first position and retracted within the body in a second position; and a plurality of conductive wires respectively connected to said electrodes for transmission of recorded signals.

9. The plunge electrode of claim 8, wherein each of said moveable electrodes is in a ball shape.

10. The plunge electrode of claim 8, wherein said conductive wires and said electrodes are coated with an insulating cover except out-exposed tips of said electrodes.

11. The plunge electrode of claim 9, wherein said moveable ball electrodes fit respectively in holes formed along the body, each of said holes being surrounded by a flexible sealing ring in conformity with the ball shape electrode.

12. The plunge electrode of claim 8, wherein said electrode adjusting means include an actuating rod of two sections linked by a crank connection, and a plurality of arms with two ends respectively pivotally attached to the actuating rod and an inner wall of the body opposite to the moveable electrodes.

13. The plunge electrode of claim 8, wherein said adjusting means include a gas bag to be filled with controllable gas from an outer source so as to support and push out the moveable electrodes in said positions.

14. The plunge electrode of claim 8, wherein said soldered and moveable electrodes are different in size.

* * * * *